(12) United States Patent
Yeh et al.

(10) Patent No.: US 11,665,238 B2
(45) Date of Patent: May 30, 2023

(54) METHOD AND SYSTEM FOR DATA TRANSMISSION BETWEEN A SENSOR DEVICE AND AN ELECTRONIC DEVICE

(71) Applicant: BIONIME CORPORATION, Taichung (TW)

(72) Inventors: Chih-Lung Yeh, Taichung (TW); Cheng-Wei Lu, Taichung (TW); Yung-Feng Lai, Taichung (TW); Guan-Yu Lu, Taichung (TW); Yuan-Chieh Lin, Taichung (TW)

(73) Assignee: BIONIME CORPORATION, Taichung (TW)

( * ) Notice: Subject to any disclaimer, the term of this patent is extended or adjusted under 35 U.S.C. 154(b) by 84 days.

(21) Appl. No.: 16/745,905

(22) Filed: Jan. 17, 2020

(65) Prior Publication Data
US 2020/0314182 A1 Oct. 1, 2020

(30) Foreign Application Priority Data
Mar. 29, 2019 (TW) .................................. 108111251

(51) Int. Cl.
| | |
|---|---|
| *H04L 67/12* | (2022.01) |
| *H04W 76/15* | (2018.01) |
| *A61B 5/00* | (2006.01) |
| *H04L 12/18* | (2006.01) |
| *H04L 67/306* | (2022.01) |
| *H04W 12/037* | (2021.01) |

(Continued)

(52) U.S. Cl.
CPC ............ *H04L 67/12* (2013.01); *A61B 5/0002* (2013.01); *H04L 12/18* (2013.01); *H04L 67/306* (2013.01); *H04W 12/037* (2021.01); *H04W 76/15* (2018.02); *A61B 5/14532* (2013.01); *H04W 4/80* (2018.02)

(58) Field of Classification Search
CPC ....... H04W 4/38; A61B 5/0002; G16H 40/63; H04L 7/0012; G06F 21/31; G06F 1/10; G07C 2009/0092
See application file for complete search history.

(56) References Cited

U.S. PATENT DOCUMENTS

| | | | |
|---|---|---|---|
| 10,171,935 B1* | 1/2019 | Reyes ..................... | G06Q 50/22 |
| 2005/0027182 A1* | 2/2005 | Siddiqui ................ | G16H 20/17 |
| | | | 128/903 |

(Continued)

FOREIGN PATENT DOCUMENTS

KR    10-2014-0142146 A    12/2014

OTHER PUBLICATIONS

European Communication pursuant to Article 94(3) EPC for European Application No. 20166139.4, dated Feb. 8, 2022.

*Primary Examiner* — Mahran Y Abu Roumi
(74) *Attorney, Agent, or Firm* — Birch, Stewart, Kolasch & Birch, LLP

(57) ABSTRACT

A method for data transmission between a sensor device and an electronic device includes: broadcasting, by the sensor device, a beacon dataset and a sensor dataset associated with the beacon dataset; in receipt of the beacon dataset, determining, by the electronic device, whether to receive the sensor dataset associated with the beacon dataset; and when it is determined to receive the sensor dataset associated with the beacon dataset, operating, by the electronic device, in a scan mode so as to receive the sensor dataset associated with the beacon dataset.

8 Claims, 4 Drawing Sheets

(51) Int. Cl.
*H04W 4/80* (2018.01)
*A61B 5/145* (2006.01)

(56) References Cited

U.S. PATENT DOCUMENTS

| | | | | |
|---|---|---|---|---|
| 2007/0255125 A1* | 11/2007 | Moberg | ............... | G16H 20/17 600/365 |
| 2007/0255348 A1* | 11/2007 | Holtzclaw | ............ | G16H 40/67 607/60 |
| 2014/0112315 A1* | 4/2014 | Yokoo | ............... | H04W 74/02 370/336 |
| 2014/0278220 A1* | 9/2014 | Yuen | ............... | A61B 5/681 702/150 |
| 2015/0080746 A1* | 3/2015 | Bleich | ............... | G16H 20/30 600/479 |
| 2015/0097671 A1 | 4/2015 | Laflen et al. | | |
| 2015/0119651 A1* | 4/2015 | Grubis | ............... | A61B 5/01 128/202.13 |
| 2015/0119733 A1* | 4/2015 | Grubis | ............ | A61B 5/02055 600/509 |
| 2015/0190100 A1* | 7/2015 | Fox | ............... | G16H 40/63 340/539.12 |
| 2016/0038675 A1* | 2/2016 | Estes | ............... | A61M 5/1723 604/151 |
| 2016/0269168 A1* | 9/2016 | Carstens | ............... | G07F 17/13 |
| 2017/0026788 A1* | 1/2017 | Kostka | ............ | G06Q 30/0267 |
| 2017/0265164 A1 | 9/2017 | Wiser | | |
| 2018/0027495 A1* | 1/2018 | Song | ............... | G06F 1/3206 455/343.2 |
| 2018/0177397 A1* | 6/2018 | Kall | ............... | A61B 5/684 |
| 2018/0206177 A1 | 7/2018 | Daoura et al. | | |
| 2018/0288563 A1* | 10/2018 | Krzych | ............... | H04W 4/021 |
| 2019/0014518 A1* | 1/2019 | Fujita | ............... | H04W 36/14 |
| 2019/0023528 A1 | 1/2019 | Franco et al. | | |
| 2019/0028997 A1 | 1/2019 | Inoue et al. | | |
| 2019/0098555 A1* | 3/2019 | Winterton | ............ | H04W 40/244 |
| 2019/0215771 A1* | 7/2019 | Kim | ............... | H04W 52/0229 |
| 2019/0336055 A1* | 11/2019 | Shah | ............... | A61B 5/681 |
| 2020/0100086 A1* | 3/2020 | Curticapean | ............ | H04B 17/318 |
| 2020/0203012 A1* | 6/2020 | Kamath | ............... | A61B 5/002 |
| 2020/0389757 A1* | 12/2020 | Kerr | ............... | G06Q 30/0269 |

* cited by examiner

METHOD AND SYSTEM FOR DATA TRANSMISSION BETWEEN A SENSOR DEVICE AND AN ELECTRONIC DEVICE

CROSS-REFERENCE TO RELATED APPLICATION

This application claims priority of Taiwanese Patent Application No. 108111251, filed on Mar. 29, 2019.

FIELD

The disclosure relates to a mechanism for data transmission, and more particularly to a method and a system for data transmission between a sensor device and an electronic device.

BACKGROUND

U.S. Patent Application Publication No. 2018/0060529 discloses a network topology for an insulin pump system. In the system, a controller of an insulin delivery device is configured to establish a first network connection with one or more peripheral devices, and to establish a second network connection with a mobile computing device. The insulin delivery device is controlled to administer dosages of insulin to a patient. The peripheral devices (e.g., a blood glucose meter (BGM), a continuous glucose monitor (CGM), etc.) are adapted to generate data related to blood glucose levels of the patient and to transmit the data wirelessly over the first network connection. A mobile application installed on the mobile computing device is programmed to communicate with the controller over the second network connection. In the U.S. Publication, the first network connection and the second network connection are embodied using Bluetooth® low energy (BLE). After the patient data has been transmitted from the peripheral devices to the insulin delivery device, the first network connection may be terminated.

It is noted that in the U.S. Publication, in order to be able to receive the patient data from multiple devices, multiple connections among the devices may be established and terminated repeatedly.

SUMMARY

Therefore, an object of the disclosure is to provide a method for data transmission between a sensor device and an electronic device.

According to one embodiment of the disclosure, the method for data transmission between a sensor device and an electronic device includes:
broadcasting, by the sensor device, a beacon dataset and a sensor dataset that is associated with the beacon dataset, the sensor dataset being generated by the sensor device and including data detected by the sensor device; in receipt of the beacon dataset, determining, by the electronic device, whether to receive the sensor dataset associated with the beacon dataset; and when it is determined to receive the sensor dataset associated with the beacon dataset, the electronic device operating in a scan mode so as to receive the sensor dataset associated with the beacon dataset.

Another object of the disclosure is to provide a system that is configured to implement the above-described method.

According to one embodiment of the disclosure, the system for data transmission includes:
a sensor device that is configured to broadcast a beacon dataset and a sensor dataset that is associated with the beacon dataset, the sensor dataset being generated by said sensor device and including data detected by said sensor device; and
an electronic device that is configured to
determine, in receipt of the beacon dataset, whether to receive the sensor dataset associated with the beacon dataset, and
when it is determined to receive the sensor dataset associated with the beacon dataset, operate in a scan mode so as to receive the sensor dataset associated with the beacon dataset.

One effect of the disclosure is that, by using the beacon dataset to determine whether to receive the corresponding sensor dataset, the electronic device operates in the scan mode only when it is determined that the sensor dataset is to be received, and stays in the standby mode the remaining time. That is to say, while the sensor device broadcasts the sensor data that propagates in the air, the electronic device may be capable of receiving the sensor data by switching to the scan mode. As such, the sensor data may be transmitted without a connection being established between the electronic device and the sensor device.

In other words, in the data transmitting procedure, the electronic device is not required to establish a pairing and a one-to-one connection with the sensor device. In this manner, the power consumed by the data transmitting procedure may be significantly reduced.

BRIEF DESCRIPTION OF THE DRAWINGS

Other features and advantages of the disclosure will become apparent in the following detailed description of the embodiments with reference to the accompanying drawings, of which.

DETAILED DESCRIPTION

Figure 1:
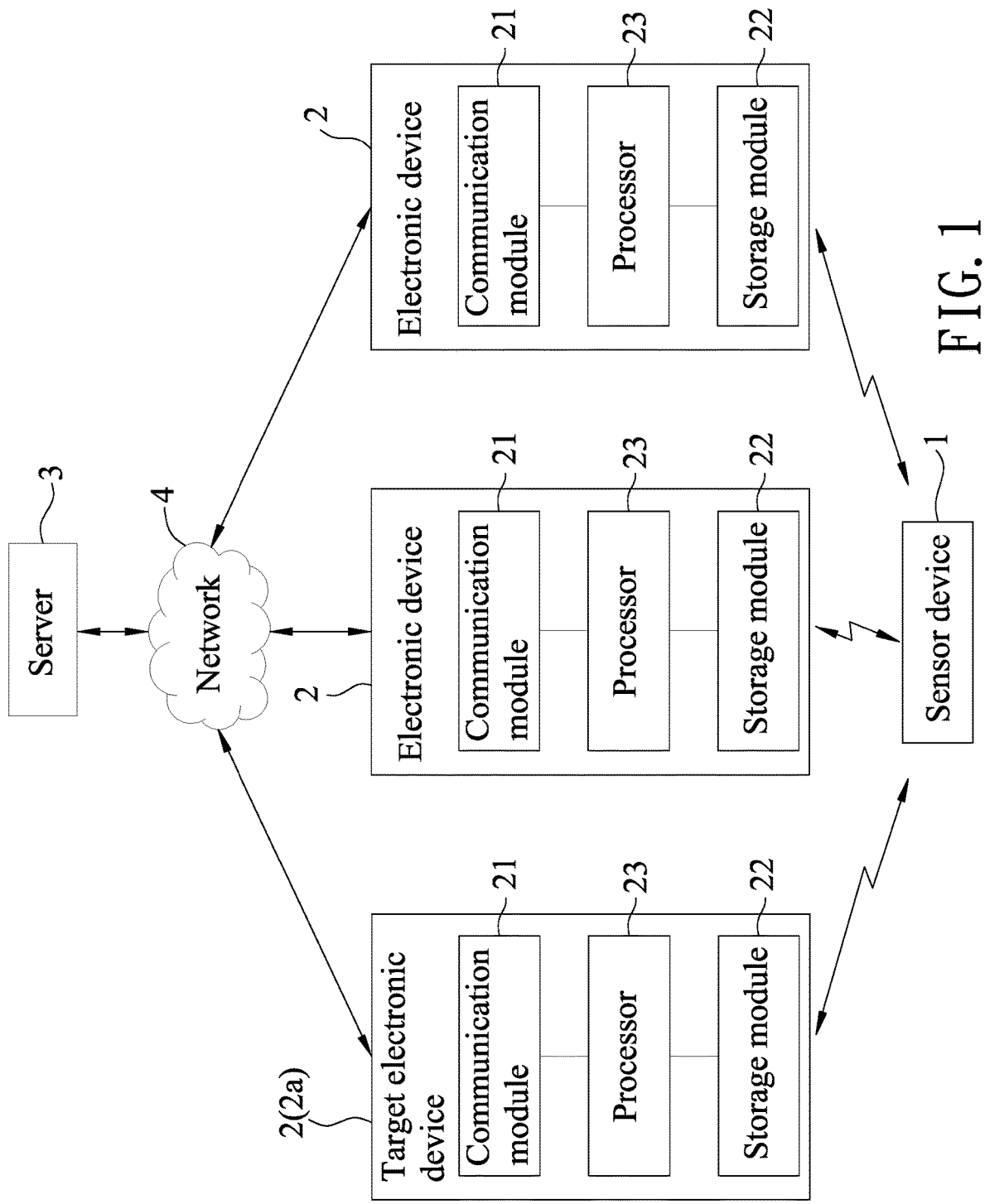
FIG. 1 is a block diagram illustrating a system for data transmission according to one embodiment of the disclosure.

Before the disclosure is described in greater detail, it should be noted that where considered appropriate, reference numerals or terminal portions of reference numerals have been repeated among the figures to indicate corresponding or analogous elements, which may optionally have similar characteristics.

FIG. 1 is a block diagram illustrating a system for data transmission according to one embodiment of the disclosure. In this embodiment, the system includes a sensor device 1, a plurality of electronic devices 2 and a server 3.

The sensor device 1 may be embodied using a continuous glucose monitor (CGM) that is configured to detect a physiologic parameter (e.g., blood glucose levels) associated with a test subject (e.g., a patient), and includes a microprocessor that is configured to generate a sensor dataset and a beacon dataset that are associated with each other. Once the sensor device 1 obtains a detected value of the physiologic parameter at a time instance, the sensor device 1 generates a corresponding sensor dataset. Each sensor dataset includes at least a detected value of the physiologic parameter detected by the sensor device 1, and a time instance associated with the detected value (indicating a time at which the detected value was obtained). In addition, the sensor device 1 may further include a transmitter that supports Bluetooth® low energy (BLE) transmission.

In use, the microcontroller is configured to control the transmitter to broadcast the beacon dataset and the sensor dataset that is associated with the beacon dataset.

Specifically, the microcontroller is configured to control the transmitter to broadcast the beacon dataset and the sensor dataset periodically.

In some embodiments, a plurality of detected values of the physiologic parameter associated with the test subject may have been obtained by the sensor device 1 at different time instances, respectively. In such a case, each sensor dataset generated by the microcontroller may incorporate all previously-obtained detected values of the physiologic parameter, or a set of newest ones of the detected values of the physiologic parameter, as of the time the sensor dataset is generated.

For example, the sensor dataset may include a number N of most recent detected values of the physiologic parameter associated with the test subject (N≥2), and the number N of time instances respectively associated with the N number of detected values of the physiologic parameter. Each of the time instances indicates a time at which the associated detected value of the physiologic parameter was obtained.

Figure 4:
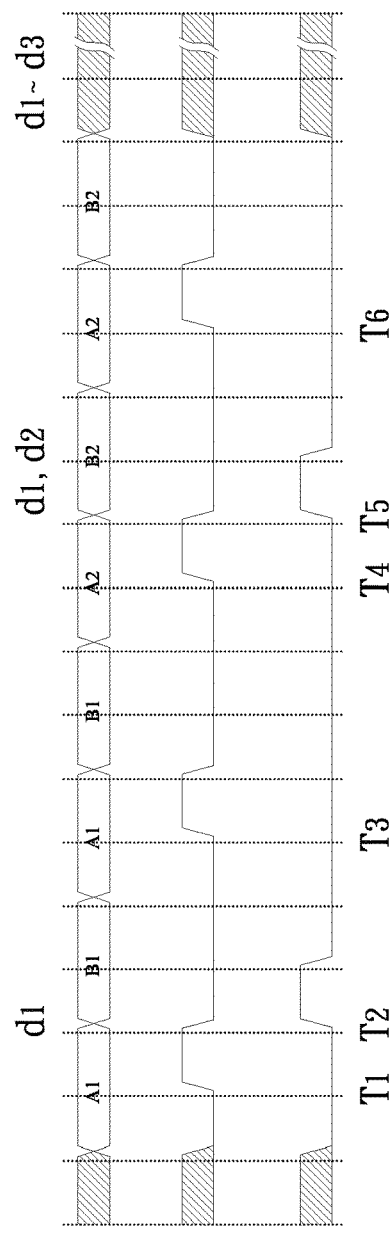
FIG. 4 is a logic signal diagram illustrating operations of an electronic device during the data transmitting procedure.

In one example as shown in FIG. 4, two sensor datasets (B1 and B2) and two beacon datasets (A1 and A2) are generated. In this example, the beacon dataset A1 is associated with the sensor dataset B1, and the beacon dataset A2 is associated with the sensor dataset B2. The beacon dataset A1 and the sensor dataset B1 are generated earlier than the beacon dataset A2 and the sensor dataset B2. The sensor dataset B1 may include a detected value of the physiologic parameter and a time instance.

After the beacon dataset A1 and the sensor dataset B1 are generated, the microcontroller is configured to control the transmitter to broadcast the beacon dataset A1 and the sensor dataset B1 in said order. The beacon dataset A1 and the sensor dataset B1 may be broadcasted repeatedly (e.g., periodically) until another (new) detected value of the physiologic parameter and a corresponding time instance are obtained.

In response, the beacon dataset A2 and the sensor dataset B2 are generated. The sensor dataset B2 may incorporate the newly-detected value of the physiologic parameter and the corresponding time instance, and the detected value and the time instance originally included in the sensor dataset B1.

After the beacon dataset A2 and the sensor dataset B2 are generated, the microcontroller is configured to control the transmitter to broadcast the beacon dataset A2 and the sensor dataset B2 in said order.

Each of the electronic devices 2 may be embodied using a personal computer (PC), a laptop, a tablet, a mobile device (e.g., a smartphone), and includes a communication module 21, a storage module 22, and a processor 23. In embodiments, the electronic devices 2 may be owned by a same user or different users.

The processor 23 may include, but not limited to, a single core processor, a multi-core processor, a dual-core mobile processor, a microprocessor, a microcontroller, a digital signal processor (DSP), a field-programmable gate array (FPGA), an application specific integrated circuit (ASIC), a radio-frequency integrated circuit (RFIC), etc.

The communication module 21 may include a short-range wireless communication module supporting a short-range wireless communication network using a wireless technology of Bluetooth® and/or Wi-Fi, BLE, etc., and a mobile communication module supporting telecommunication using Long-Term Evolution (LTE), the third generation (3G) and/or fourth generation (4G) of wireless mobile telecommunications technology, and/or the like.

The storage module 22 may be embodied using one or more of a hard disk, a solid-state drive (SSD), flash memory or other non-transitory storage medium. The storage module 22 stores a software application therein. The software application includes instructions that, when executed by the processor 23, causes the processor 23 to implement a number of operations as described in the succeeding paragraphs. In other words, the processor 23 of each of the electric devices 2 is configured to perform the operations/actions described in connection therewith in the succeeding paragraphs.

The server 3 is configured to communicate with the electronic devices 2 over a network 4 (e.g., the Internet) and is a cloud server in this embodiment. The server 3 stores a number of user profiles, each being associated with a user of at least one of the electronic devices 2. Each of the user profiles may include account information associated with an account of the user (e.g., an account number and a password), user information associated with the user, and a key that is associated with the account. In use, each of the electronic devices 2 may be operated by a user executing an application to log into the server 3 using the account number and the password, and afterward, the electronic devices 2 may be configured to transmit data that is associated with the account of the user.

According to one embodiment of the disclosure, there is provided a method for data transmission between the sensor device 1 and one of the electronic devices 2. In this embodiment, the method is implemented by the system of FIG. 1, and includes an encryption key transmitting procedure and a data transmitting procedure. It is noted that the method may be implemented between the sensor device 1 and any one of the electronic devices 2, and in the following paragraphs, a representative one of the electronic devices 2a (which may be referred to as a target electronic device) is used as an example.

Figure 2:
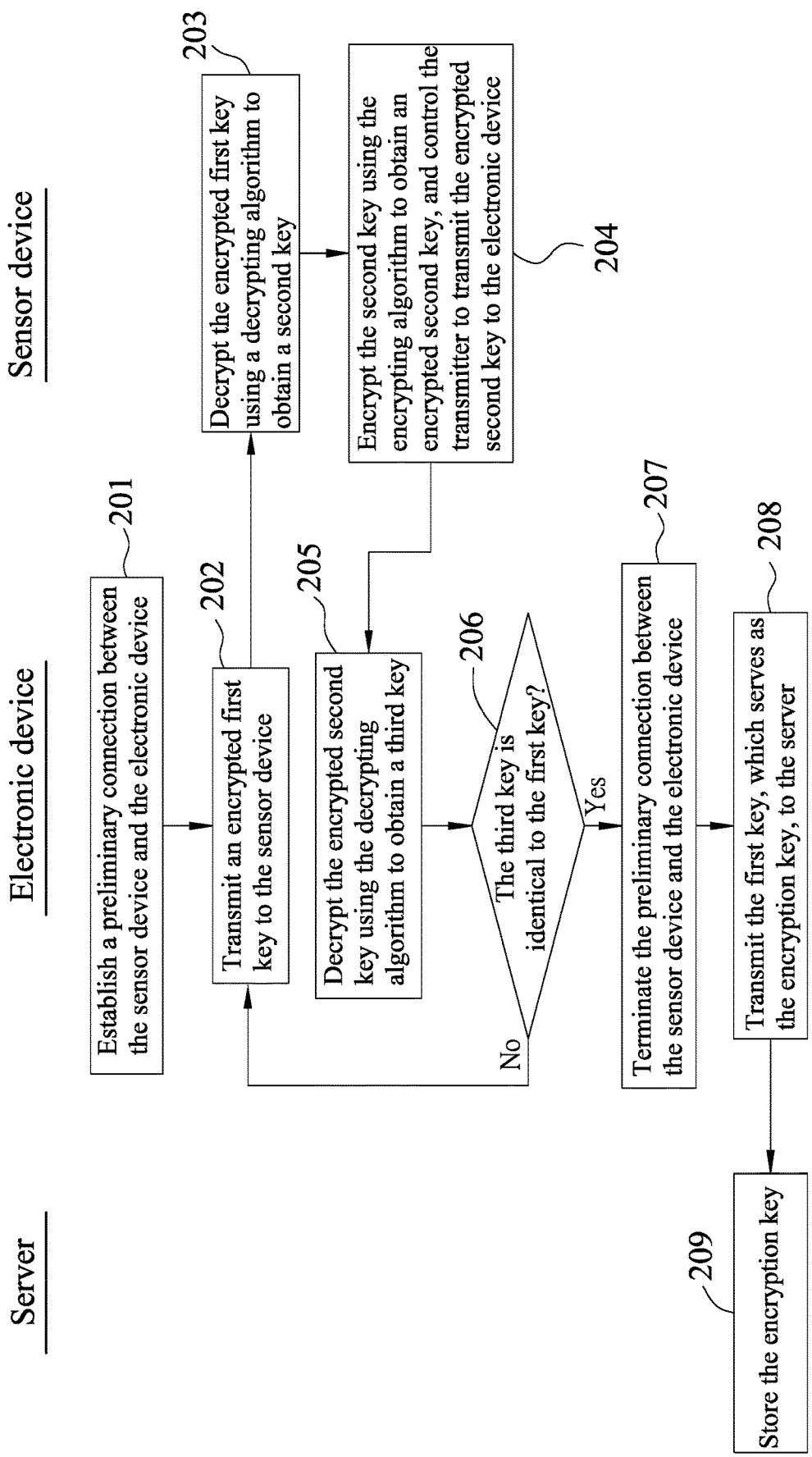
FIG. 2 is a flow chart illustrating an encryption key transmitting procedure of a method for data transmission according to one embodiment of the disclosure.

FIG. 2 is a flow chart illustrating steps of the encryption key transmitting procedure, according to one embodiment of the disclosure. The encryption key transmitting procedure is implemented prior to transmission of actual data, so as to enable the sensor device 1 and the electronic device 2a to encrypt and decrypt the data to be transmitted using an encryption key.

In step 201, the processor 23 of the electronic device 2a establishes a preliminary connection between the sensor device 1 and the electronic device 2a. The preliminary connection may be done when the sensor device 1 is to be used for the first time, and may be implemented using a peer-to-peer connection such as BLE or other wired/wireless connections.

In step 202, the processor 23 of the electronic device 2a transmits an encrypted first key to the sensor device 1. In this embodiment, the encrypted first key was obtained by encrypting a first key using an encrypting algorithm. The first key may be a user-provided key inputted by the user using the electronic device 2a, or a key that is generated by the electronic device 2a or the server 3. The encrypting algorithm may be one conforming with the Advanced Encryption Standard (AES) In step 203, in response to receipt of the encrypted first key, the microprocessor of the sensor device 1 decrypts the encrypted first key using a decrypting algorithm to obtain a second key. In this embodiment, the decrypting algorithm may be one conforming with the AES.

In step 204, the microprocessor of the sensor device 1 encrypts the second key using the encrypting algorithm to obtain an encrypted second key, and controls the transmitter to transmit the encrypted second key to the electronic device 2a.

In step 205, the processor 23 of the electronic device 2a decrypts the encrypted second key using the decrypting algorithm to obtain a third key.

In step 206, the processor 23 of the electronic device 2a compares the third key and the first key, and determines whether the third key is identical to the first key. When it is determined that the third key is identical to the first key, the electronic device 2a determines that the sensor device 1 has obtained the first key, and the flow proceeds to step 207. Otherwise, the electronic device 2a determines that an error has occurred during the encryption key transmitting procedure, and the flow goes back to step 202. It should be noted that, when it is determined that the third key is identical to the first key, it may be deduced that the first key, the second key and the third key must be identical to one another.

In step 207, the processor 23 of the electronic device 2a terminates the preliminary connection between the sensor device 1 and the electronic device 2a after determining that the sensor device 1 has obtained the first key (i.e., the second key).

In step 208, the processor 23 of the electronic device 2a controls the communication module 21 to transmit the first key, which serves as the encryption key, to the server 3. Afterwards, the sensor device 1 encrypts the sensor dataset using the second key serving as the encryption key, and the electronic device 2 decrypts the sensor dataset using the first key serving as the encryption key.

In step 209, the server 3 stores the encryption key, and associates the encryption key with one of the user profiles that is associated with the user of the electronic device 2a. In this manner, the user of the electronic device 2a may operate another one of the electronic devices 2 to log onto the server 3 to obtain the encryption key.

While in this embodiment, the encryption key transmitting procedure as shown in FIG. 2 is implemented in order to enhance the security of the encryption key, the encryption key may be directly transmitted from the electronic device 2a to the sensor device 1 in other embodiments. After the encryption key has been transmitted, the preliminary connection between the sensor device 1 and the electronic device 2a may be terminated.

Figure 3:
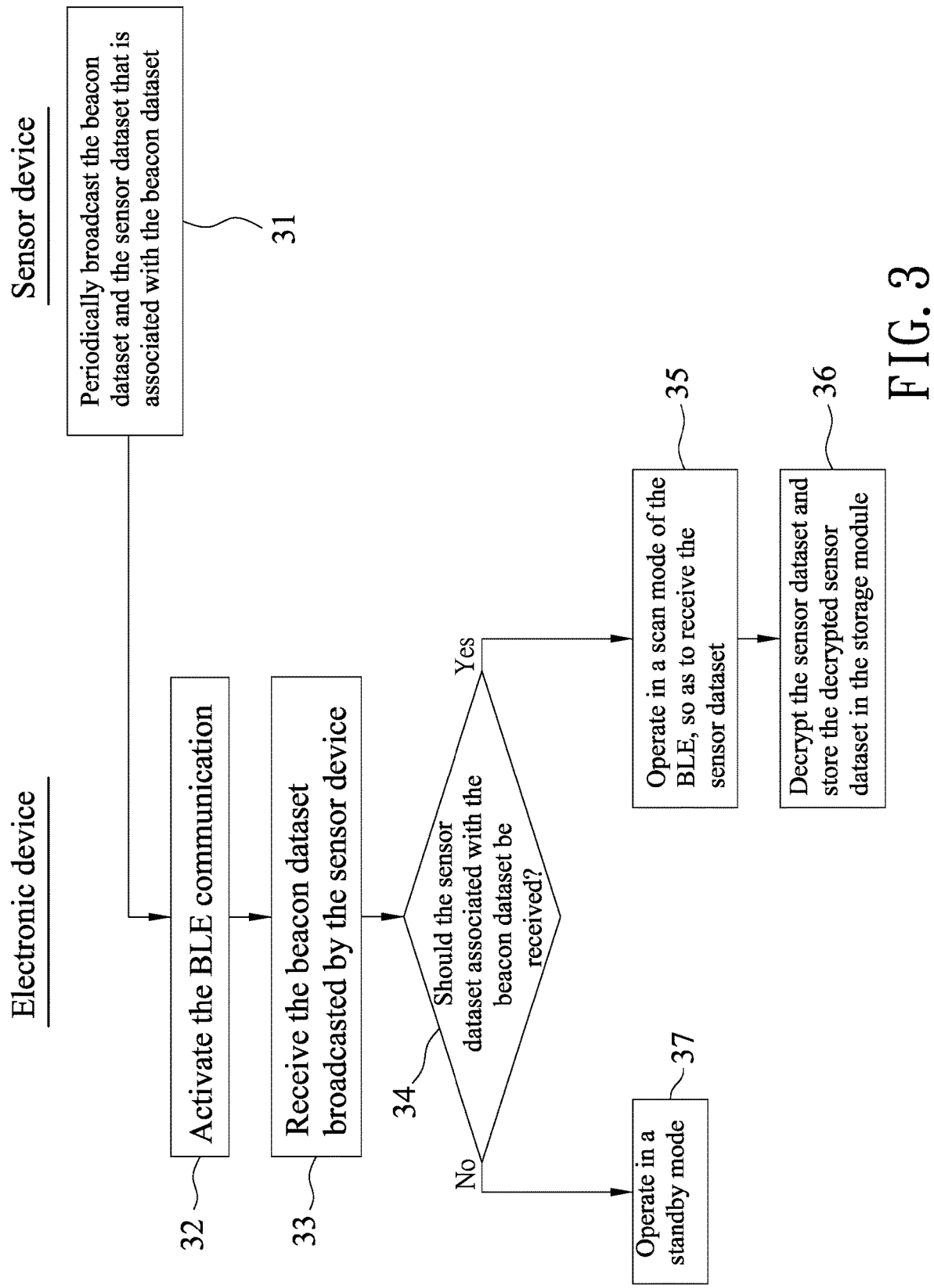
FIG. 3 is a flow chart illustrating a data transmitting procedure of the method for data transmission according to one embodiment of the disclosure.

FIG. 3 is a flow chart illustrating steps of the data transmitting procedure according to one embodiment of the disclosure. In this embodiment, the data transmitting procedure is implemented by the system of FIG. 1, and may be done between the sensor device 1 and any one of the electronic devices 2 (e.g., the electronic device 2a).

In step 31, after at least one sensor dataset and a corresponding beacon dataset have been generated, the microprocessor of the sensor device 1 controls the transmitter to repeatedly (e.g., periodically) broadcast the beacon dataset and the sensor dataset that is associated with the beacon dataset. Specifically, the broadcasting is implemented using BLE, and the sensor dataset broadcasted is encrypted using the encryption key (i.e., the second key) and the encrypting algorithm.

In step 32, the processor 23 of the electronic device 2a controls the communication module 21 to activate the BLE communication, such that when the electronic device 2a is within a communication range of the sensor device 1, the communication module 21 is capable of receiving the beacon dataset broadcasted by the sensor device 1.

In step 33, the communication module 21 of the electronic device 2a receives the beacon dataset broadcasted by the sensor device 1. In some embodiments, the beacon dataset thus received is then stored in the storage module 22.

In step 34, the processor 23 of the electronic device 2a determines whether to receive the sensor dataset associated with the beacon dataset received in step 33.

Specifically, the processor 23 of the electronic device 2a may be triggered by the receipt of the beacon dataset to execute a procedure to determine whether the beacon dataset has been received by the electronic device 2a before, for example, by accessing the storage module 22 to determine whether a beacon dataset already stored in the storage module 22 is the same as the beacon dataset received in step 33. When the beacon dataset stored in the storage module 22 is the same as the beacon dataset received, the processor 23 may determine that the associated sensor dataset has also been received by the electronic device 2a previously, and therefore is not required to be received again and the broadcasted sensor dataset may be ignored. In such a case, the flow proceeds to step 37.

Otherwise, it is determined that the sensor dataset associated with the beacon dataset has not been received by the electronic device 2a before and therefore should be received, and the flow proceeds to step 35.

In step 35, the processor 23 of the electronic device 2a controls the communication module 21 to operate in a scan mode of the BLE. It is noted that in the scan mode, the communication module 21 is capable of receiving the sensor dataset currently broadcasted by the sensor device 1.

In step 36, in response to receipt of the sensor dataset, the processor 23 of the electronic device 2a decrypts the sensor dataset using the encryption key (i.e., the first key) and the decrypting algorithm, and stores the decrypted sensor dataset in the storage module 22. Afterward, the flow proceeds to step 37.

In step 37, the processor 23 of the electronic device 2a controls the communication module 21 to operate in a standby mode (e.g., deactivate the BLE communication). As such, the sensor dataset is successfully transmitted to the electronic device 2a. Specifically, by employing the above mechanism to transmit data, the electronic device 2a is not required to establish a pairing and a peer-to-peer connection with the sensor device 1 during the data transmitting procedure. In this manner, the power consumed by the data transmitting procedure may be significantly reduced.

It is noted that the above steps may be applied in a similar manner to transmit the sensor dataset to each of the electronic devices 2.

Referring to the example of FIG. 4, a number n of sensor datasets and a number n of beacon datasets are generated. The sensor device 1 controls the transmitter to periodically broadcast the beacon dataset Ai and the sensor dataset Bi, where i=1 to n. After the beacon dataset A1 and the sensor dataset B1 are generated, the microcontroller controls the transmitter to broadcast the beacon dataset A1 and the sensor dataset B1 in said order.

At the time instance T1, the electronic device 2a is initially in the standby mode (shown in the form of a logic signal at 0). When the communication module 21 first receives the beacon dataset A1 as a trigger to "wake up"

from the standby mode (shown in the form of a logic signal going from 0 to 1), the processor 23 determines whether the beacon dataset A1 has been received (step 34).

At the time instance T2, the processor 23 determines that the beacon dataset A1 has not been received yet, and thus controls the communication module 21 to operate in the scan mode of the BLE (shown in the form of the logic signal going from 0 to 1), so as to receive the sensor dataset B1 broadcasted by the sensor device 1 (step 35). Afterward, the electronic device 2a is switched to the standby mode (shown in the form of a logic signal going from 1 to 0).

The beacon dataset A1 and the sensor dataset B1 may be broadcasted repeatedly (e.g., periodically) before the beacon dataset A2 and the sensor dataset B2 are generated.

At time instance T3, when the processor 23 activates the BLE communication of the communication module 21, the communication module 21 first receives the beacon dataset A1 as a trigger, and proceeds to determine whether the beacon dataset A1 has been received previously.

At this time, since the beacon dataset A1 has been received previously, the electronic device 2a determines that the corresponding sensor dataset B1 has also been received previously and no data transmission is needed. Therefore, the electronic device 2a remains in the standby mode, and no data is transmitted from the sensor device 1 to the electronic device 2a.

After the beacon dataset A2 and the sensor dataset B2 are generated, the microcontroller is then configured to control the transmitter to broadcast the beacon dataset A2 and the sensor dataset B2 in said order.

At time instance T4, the communication module 21 receives the beacon dataset A2 as a trigger to "wake up" from the standby mode, and the processor 23 determines whether the beacon dataset A2 has been received (step 34).

At time instance T5, the processor 23 determines that the beacon dataset A2 has not been received yet, and thus controls the communication module 21 to operate in the scan mode of the BLE, so as to receive the sensor dataset B2 broadcasted by the sensor device 1 (step 35). Afterward, the electronic device 2a is switched to the standby mode.

Then, at time instance T6, the communication module 21 first receives the beacon dataset A2 as a trigger to "wake up" from the standby mode, and proceeds to determine whether the beacon dataset A2 has been received.

At this time, since the beacon dataset A2 has already been received, the electronic device 2a determines that the corresponding sensor dataset B2 has also already been received and no data transmission is needed. As a result, the electronic device 2a is configured to remain in the standby mode, and no data is transmitted from the sensor device 1 to the electronic device 2a.

It is noted that while two sets of sensor datasets and beacon datasets are presented in the example of FIG. 4, additional sensor dataset(s) and beacon dataset(s) may be generated at different time instances and broadcasted by the sensor device 1.

It is noted that, since the sensor device 1 is configured to broadcast the sensor datasets and beacon datasets, when a plurality of electronic devices 2 are in the communication range of the sensor device 1 and are configured in a similar manner as the electronic device 2a, each of the plurality of electronic devices 2 may be able to receive the sensor datasets simultaneously, and to use the encryption key to obtain the decrypted sensor datasets.

To sum up, the embodiments of the disclosure provide a method and system for data transmission between the sensor device 1 and one or more electronic devices 2. By using the beacon dataset to determine whether to receive the corresponding sensor dataset, the electronic device 2 operates in the scan mode only when it is determined that the sensor dataset is to be received, and stays in the standby mode in other time periods. That is to say, while the sensor device 1 broadcasts the sensor data that propagates in the air, the electronic device 2 may be capable of receiving the sensor data by switching to the scan mode. As such, the sensor data may be transmitted without a connection being established between the electronic device 2 and the sensor device 1.

In other words, in the data transmitting procedure, the electronic device 2 is not required to establish a pairing and a one-to-one connection with the sensor device 1. In this manner, the power consumed by the data transmitting procedure may be significantly reduced.

Moreover, prior to the data transmitting procedure, the electronic device 2 may first establish the preliminary connection with the sensor device 1 for transmitting the encryption key thereto. Afterward, the sensor dataset to be broadcasted by the sensor device 1 may be encrypted. In such a manner, although the encrypted sensor dataset may be received by other devices, the encrypted sensor dataset cannot be decrypted by those devices without the encryption key and the decrypting algorithm. As such, the data transmitting procedure may be more secure while maintaining a low power consumption.

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A method for data transmission between a sensor device and an electronic device, comprising steps of:
broadcasting, by the sensor device, a beacon dataset and a sensor dataset that corresponds to the beacon dataset, the sensor dataset being generated by the sensor device and including data detected by the sensor device, the sensor dataset including at least two most recent detected values of a physiologic parameter associated with a test subject;
in receipt of the beacon dataset, determining, by the electronic device, whether to receive the sensor dataset that corresponds to the beacon dataset; and
when it is determined to receive the sensor dataset that corresponds to the beacon dataset, operating, by the electronic device, in a scan mode so as to receive the sensor dataset that corresponds to the beacon dataset;

wherein:

the step of broadcasting a beacon dataset and a sensor dataset is to periodically broadcast the beacon dataset and the sensor dataset;

the step of determining whether to receive the sensor dataset that corresponds to the beacon dataset includes determining whether the beacon dataset has been received before by the electronic device, and determining to receive the sensor dataset that corresponds to the beacon dataset when it is determined that the beacon dataset has not been received by the electronic device before; and the sensor data is transmitted without a pairing between the electronic device and the sensor device and a one-to-one connection being established between the electronic device and the sensor device, wherein the method further comprises, prior to the step of broadcasting, steps of:

establishing, by the electronic device, a preliminary connection between the sensor device and the electronic device;

obtaining, by the sensor device, an encryption key from the electronic device; and encrypting, by the sensor device, the sensor dataset using the encryption key wherein the method further comprises the following steps of;

transmitting, by the electronic device to the sensor device, and encrypted first key that was created by encrypting a first key using an encrypting algorithm;

decrypting, by the sensor device, the encrypted first key using a decrypting algorithm to obtain a second key;

encrypting, by the sensor device, the second key using the encrypting algorithm to obtain an encrypted second key, and transmitting the encrypted second key to the electronic device, decrypting, by the electronic device, the encrypted second key using the decrypting algorithm to obtain a third key;

comparing, by the electronic device, the third key and the first key;

when it is determined that the third key is identical to the first key, determining, by the electronic device, that the sensor device has obtained the encryption key;

terminating, by the electronic device, the preliminary connection between the sensor device and the electronic device after determining that the sensor device has obtained the first key, encrypting, by the sensor device, the sensor dataset using the second key serving as the encryption key; and decrypting, by the electronic device, the sensor dataset using the first key serving as the decrypting key.

2. The method of, the electronic device communicating with a server via a network, the server storing a user profile associated with a user of the electronic device, the user profile including account information of the user, the method further comprising:

transmitting, by the electronic device, the first key to the server, so as to enable the server to associate the first key with the user profile.

3. The method of claim 1, further comprising storing the sensor dataset by the electronic device.

4. The method of claim 1, further comprising: when it is determined not to receive the sensor dataset associated with the beacon dataset, the electronic device operating in a standby mode.

5. A system for data transmission comprising:

a sensor device that is configured to broadcast a beacon dataset and a sensor dataset that corresponds to the beacon dataset, the sensor dataset being generated by said sensor device and including data detected by said sensor device, wherein said sensor device is configured to generate the sensor dataset to include at least two most recent detected values of a physiologic parameter associated with a test subject; and an electronic device that is configured to determine, in receipt of the beacon dataset, whether to receive the sensor dataset that corresponds to the beacon dataset, and when it is determined to receive the sensor dataset that corresponds to the beacon dataset, operate in a scan mode so as to receive the sensor dataset that corresponds to the beacon dataset;

wherein:

said sensor device is configured to periodically broadcast the beacon dataset and the sensor dataset;

said electronic device is configured to determine whether the beacon dataset has been received by said electronic device before, and determine to receive the sensor dataset that corresponds to the beacon dataset when it is determined that the beacon dataset has not been received by said electronic device before;

the sensor data is transmitted without a pairing between the electronic device and the sensor device and a one-to-one connection being established between said electronic device and said sensor device;

said electronic device is configured to establish a preliminary connection between said sensor device and said electronic device;

said sensor device is configured to, in response to an encryption key from said electronic device, encrypt the sensor dataset using the encryption key;

said electronic device is configured to transmit, to said sensor device, and encrypted first key that was created by encrypting a first key using an encrypting algorithm;

said sensor device is configured to decrypt the encrypted first key using a decrypting algorithm to obtain a second key, to encrypt the second key using the encrypting algorithm to obtain an encrypted second key, and to transmit the encrypted second key to said electronic device;

said electronic device is configured to decrypt the encrypted second key using the decrypting algorithm to obtain a third key, and to compare the third key and the first key;

said electronic device is configured to, when it is determined that the third key is identical to the first key, determine that said sensor device has obtained the encryption key;

said electronic device is configured to, after determining that said sensor device has obtained the first key, terminate the preliminary connection between said sensor device and said electronic device;

said sensor device is configured to encrypt the sensor dataset using the second key serving as the encrypting key; and said electronic device is configured to decrypt the sensor dataset using the first key serving as the decryption key.

6. The system of claim 5, wherein:

said electronic device communicates with a server via a network, the server storing a user profile associated with a user of said electronic device, the user profile including account information of the user;

said electronic device is configured to transmit the first key to the server, so as to enable the server to associate the first key with the user profile.

7. The system of claim 5, wherein said electronic device is further configured to store the sensor dataset therein upon receipt thereof.

8. The system of claim 5, wherein said electronic device is configured to, when it is determined not to receive the sensor dataset associated with the beacon dataset, operate in a standby mode.

* * * * *